(12) United States Patent
Sakai et al.

(10) Patent No.: US 7,645,594 B2
(45) Date of Patent: Jan. 12, 2010

(54) METHOD OF PREPARING ASSAY SAMPLE FOR DISCRIMINATING BACTERIA BY FLOW CYTOMETER

(75) Inventors: Yasuhiro Sakai, Hyogo (JP); Yasuyuki Kawashima, Hyogo (JP); Junya Inoue, Hyogo (JP); Yoshiro Ikeuchi, Hyogo (JP)

(73) Assignee: Sysmex Corporation, Hyogo (JP)

( * ) Notice: Subject to any disclaimer, the term of this patent is extended or adjusted under 35 U.S.C. 154(b) by 428 days.

(21) Appl. No.: 10/803,667

(22) Filed: Mar. 18, 2004

(65) Prior Publication Data

US 2004/0175781 A1    Sep. 9, 2004

Related U.S. Application Data

(62) Division of application No. 10/005,753, filed on Oct. 29, 2001, now Pat. No. 7,309,581.

(30) Foreign Application Priority Data

Nov. 1, 2000    (JP) ............................. 2000-334641

(51) Int. Cl.
*C12Q 1/04* (2006.01)
*G01N 1/30* (2006.01)

(52) U.S. Cl. .......................... 435/40.5; 435/34; 435/35; 436/18

(58) Field of Classification Search ................ None
See application file for complete search history.

(56) References Cited

U.S. PATENT DOCUMENTS

| 4,783,401 | A | * | 11/1988 | Horan et al. ................... 435/34 |
| 5,545,535 | A | * | 8/1996 | Roth et al. ..................... 435/34 |
| 5,656,449 | A | * | 8/1997 | Yue .............................. 435/34 |
| 5,773,592 | A | | 6/1998 | Mills |
| 5,891,731 | A | * | 4/1999 | Akai et al. ..................... 436/10 |
| 5,891,733 | A | * | 4/1999 | Inoue .......................... 436/63 |
| 7,422,870 | B2 | * | 9/2008 | Kawashima et al. ........... 435/34 |

FOREIGN PATENT DOCUMENTS

| EP | 0 882 983 A | 12/1998 |
| EP | 1136563 A2 | 9/2001 |
| GB | 826066 | 12/1959 |

OTHER PUBLICATIONS

Ernst LA, Gupta RK, Mujumdar RB, Waggoner As, Cyanine Dye Labeling Reagents for Sulfhydryl Groups, CYtometry, 1989, 10: 3-10.*
Kirk O, Pedersen FD, Fuglsang CC, Preparation and Properties of a New Type of Carbohydrate-based Cationic Surfactant, Journal of Surfactants and Detergents, 1998, 1(1): 37-40.*
Dement Publications Ltd., "New Methine Dyes are Capable of Being Effectively Excited with Economical Helium-Neon Laser Light Source with Resultant Stronger Fluorescent Intesity", JP 2000 273330A, (Fuji Photo Film Co. Ltd.), Oct. 3, 2000 Abstract.
G. P. James et al., "Urinary Nitrite and Urinary-Tract Infection", Am J. Clinical Pathol, vol. 70, 1978, pp. 671-678.
Y. Nakagawa, et al., "Characteristic Bleaching Profiles of Cyanine Dyes Depending on Active Oxygen Species in the Controlled Fenton Reaction", Biological and Pharmaceutical Bulletin, vol. 16, No. 11, 1993, pp. 1061-1064.
H. Okada, et al., "Detection of Significant Bacteriuria by Automated Urinalysis Using Flow Cytometry", Journal of Clinical Microbiology, vol. 38, No. 8, Aug. 2000, pp. 2870-2872.
S. Smith et al., "Detection of Urinary Tract Infections by Reduction of Nitroblue Tetrazolium: Technical Note", Kidney International, vol. 54. No. 4, Oct. 1998, pp. 1331-1336.

* cited by examiner

*Primary Examiner*—Cecilia Tsang
*Assistant Examiner*—Julie Ha
(74) *Attorney, Agent, or Firm*—Cohen Pontani Lieberman & Pavane LLP (57) ABSTRACT

A method of staining bacteria comprises: working a polymethine dye on a sample in the presence of a substance capable of reducing nitrite ions to stain bacteria in the sample. A method of detecting bacteria comprises the following steps of: (1) working a polymethine dye on a sample by a method as described above to stain bacteria in the sample, (2) introducing the thus treated sample into a detecting part of a flow cytometer and irradiating cells of the stained bacteria one by one with light to measure scattered light and fluorescent light emitted from each of the cells; and (3) discriminating the bacteria from other components in accordance with an intensity of a scattered light signal and an intensity of a fluorescent light signal or a pulse width reflecting the length of particles to count the bacteria.

12 Claims, 2 Drawing Sheets

METHOD OF PREPARING ASSAY SAMPLE FOR DISCRIMINATING BACTERIA BY FLOW CYTOMETER

CROSS-REFERENCE TO RELATED APPLICATION

This application is a Divisional Application which claims priority from an application filed in Japan on Nov. 1, 2000, Application No. 2000-334641. The disclosure of U.S. patent application Ser. No. 10/005,753, filed Oct. 29, 2001, now U.S. Pat. No. 7,309,581, is incorporated herein by reference.

BACKGROUND OF THE INVENTION

1. Field of the Invention

The present invention relates to a method of staining, and detecting and counting bacteria in clinical samples, in particular, bacteria in urine samples, and a diluent for bacterial stain.

2. Related Art

The number of bacteria in urine is an important parameter in clinical diagnosis to judge the presence of infection. In general, the presence of bacteria of $10^5$ or more/ml in urine is recognized as a criterion of positive urinary tract infection. If urine contains bacteria of $10^3$ or more/ml, it is diagnosed as contaminated urine (normal bacteria flora), i.e., negative urinary tract infection. If bacteria of about $10^4$/ml is observed, the diagnosis is reserved but the sample is often re-examined.

Conventionally, observation of bacteria in urine has been performed by microscopic examination of Gram stained bacteria, unstained bacteria without Gram staining treatment or fluorescence-stained bacteria.

Urine often contains contaminants such as mucus threads, crystals, amorphous salts and cell fragments that are clinically insignificant. These substances hinder the measurement of significant particles (in particular bacteria) so that it has been difficult to accurately count the number of bacteria. Actually, there has been no method of counting bacteria of about $10^4$/ml, accurately.

In the case of Gram stain, bacteria and contaminants are stained simultaneously so that counting loss of bacteria of a small number occurs frequently in the microscopic examination. Further, Gram stain includes a number of staining steps and takes time (about 15 minutes) so that working efficiency is poor.

The microscopic examination of bacteria without staining treatment can be carried out quickly, but it cannot discriminate bacteria particularly when coccus contaminants are contained.

The microscopic examination of fluorescence-stained bacteria shows better detectability than the above-mentioned two methods. However, there has not been established how to eliminate other contaminants than bacteria and to stain the bacteria quickly.

Agar medium method, which is a standard method, requires 16 hours or more to determine the bacteria number, so that it cannot be regarded as a quick method.

U.S. Pat. No. 4,622,298, and Japanese Unexamined Patent Publication No. Hei 9 (1997)-119926 and No. Hei 9 (1997)-329596 each proposes a method of detecting bacteria in a fluorescence-stained urine sample with a flow cytometer.

A polymethine dye utilizes for fluorescence staining in the above references, but some bacteria are not sufficiently stained with the polymethine dye. For example, in the case of a sample in which nitrate-reducing bacteria proliferate and produce a large amount of nitrite, nitrite ions decompose the polymethine dye so that the dye does not effectively work on the bacteria staining.

Usually, bacteria are stained well at acidic pH. Further, a urine sample which contains mucus threads is effective in the bacteria staining. However, effect of the nitrite ions is promoted at acidic pH.

SUMMARY OF THE INVENTION

An object of the present invention is to provide a method of staining, and detecting and counting bacteria which allows quick and efficient detection of bacteria even if a sample contains nitrite ions at high concentration.

The present invention provides a method of staining bacteria comprising: working a polymethine dye on a sample in the presence of a substance capable of reducing nitrite ions to stain bacteria in the sample.

Further, the present invention provides a method of detecting and counting bacteria comprising the following steps of:

(1) working a polymethine dye on a sample to stain bacteria by a method as described in the above to stain bacteria in the sample, (2) introducing the thus treated sample into a detecting part of a flow cytometer and irradiating cells of the stained bacteria one by one with light to measure scattered light and fluorescent light emitted from each of the cells; and (3) discriminating the bacteria from other components in accordance with an intensity of a scattered light signal and an intensity of a fluorescent light signal or a pulse width reflecting the length of particles to count the number of the bacteria.

Further, the present invention provides a diluent for bacterial stain comprising: a buffer for maintaining acidity; and an effective amount of a substance capable of reducing nitrite ions.

DESCRIPTION OF THE PREFERRED EMBODIMENTS

In the present invention, the sample is not particularly limited as long as it is a sample to be examined for the presence or absence of bacteria and to count a number of bacteria if the sample contains bacteria. Bacteria referred herein include bacteria which reduce nitrite and produce nitrous acid, e.g., intestinal bacteria such as *Staphyrococcus aureus*, Gram-negative facultative bacilli such as *E. coli*, *Klebsiella* sp. and *Proteus* sp., or bacteria observed in a urine sample such as *E. coli*, *Klebsiella* sp., as well as *Staphyrococcus* sp., *Pseudomonas* sp., *Serratia* sp., *Enterobacter* sp., *Enterococcus* sp., *Streptpococcus* sp. and *Citrobacter* sp. For example, the sample may be a clinical sample such as urine, blood, spinal fluid or the like. The sample may be diluted with purified water or the like two or more times, preferably 4 to 15 times, more preferably 5 to 10 times. The present invention is particularly effective for a urine sample.

The substance capable of reducing nitrite ions may be one or more kinds selected from the group comprising of: ascorbic acid, isoascorbic acid, aminomethanesulfonic acid, aminoethanesulfonic acid, glutamic acid, asparatic acid, mercaptoacetic acid, 3-mercaptopropionic acid, sulfamic acid, sulfanilic acid, sulfurous acid, pyrosulfurous acid, phosphinic acid, glycine, glutamine, asparagine, methionine, glutathione, cysteine, hydroxylamine and salts thereof; sulfanilamide; aminomethane; mercaptoethanol; thiophenol; urea and the like. Examples of the salts may generally be an alkaline salt (e.g., sodium ascorbate, sodium isoascorbate, sodium sulfite, sodium pyrosulfite, sodium phosphinate, potassium ascorbate, potassium isoascorbate, etc.) and but salts of hydroxylamine may be hydroxylamine hydrochloride, hydroxylamine sulfate, hydroxylamine phosphate, etc. With respect to the concentration thereof, it may be contained at 10 mM or more in the sample (final concentration). Preferably, ascorbic acid may be contained at 85 to 115 mM, sulfamic acid may be contained at 40 to 200 mM, cysteine, glutathione and sodium sulfite may be contained at 10 to 50 mM, respectively. Urea may be contained at 0.5 M or more, preferably at an extent where it may not cause denaturation of cells. In general, it is considered that 0.06 mg/ml of nitrite ions are produced in the presence of nitrate-reducing bacteria of $10^5$/ml. Further, proliferation of bacteria is considered to be limited up to $10^8$ to $10^9$/ml and it does not (cannot) proceed any higher. Therefore, the substance may be used in such an amount that it can reduce nitrite ions produced by bacteria of $10^5$ to $10^8$/ml.

In particular, where proliferation of nitrate-reducing bacteria occurs to produce a large amount of nitrite in the sample, the substance capable of reducing nitrite ions is used to prevent decomposition of the dye caused by the nitrite ions. As a result, dye transmissivity of bacteria is enhanced.

In order to stain bacteria effectively, the cell membrane (cell walls) of the bacteria may be damaged so that a dye enters cells easily. For example, a cationic surfactant, an anion surfactant, an ampholytic surfactant, a nonionic surfactant or the like may be used for achieving this purpose. The same purpose can also be achieved by use of an anti-bacterial/antiseptic agent (anti-bacterial agent), an organic solvent such as alcohol in addition to the surfactant. Further, sufficient stainability can be obtained by thermal damage or by damage caused by a microwave (a microwave oven, etc.). Among those mentioned above, the cationic surfactant may be suitably used since the cationic surfactant not only improves the stainability of bacteria but also dissolves/shrinks mucous fibers, erythrocytes, cell fractures and others which are present in a sample and thereby reduces their effect on detection of bacteria.

No particular limitation is given to the cationic surfactant, but preferably is used a quarternary ammonium salt represented by the following formula:

wherein $R^{10}$ is a $C_{6-18}$ alkyl group or $(C_6H_5)$—$CH_2$—; $R^{11}$, $R^{12}$ and $R^{13}$, the same or different, are a $C_{1-3}$ alkyl group or a benzyl group; $Y^-$ is a halogen ion.

The $C_{1-3}$ alkyl group may be methyl, ethyl, propyl. The $C_{6-18}$ alkyl group may be hexyl, heptyl, octyl, decyl, dodecyl, tetradecyl or the like. The halogen may be fluorine, bromine, iodine and chlorine.

For example, are suitably used hexyl trimethyl ammonium salts, octyl trimethyl ammonium salts, decyl trimethyl ammonium salts, dodecyl trimethyl ammonium salts, tetradecyl trimethyl ammonium salts, hexadecyl trimethyl ammonium salts, octadecyl trimethyl ammonium salts, benzyl trimethyl ammonium salts and the like.

Other examples of the cationic surfactant may be pyridinium salts of the following formula:

$$[(C_5H_5)N^+—(CH_2)_n—CH_3]Y^-$$

wherein n is from 7 to 17 and $Y^-$ is a halogen ion. For example, are suitably used octyl pyridinium salts, decyl pyridinium salts, dodecyl trimethyl pyridinium salts, tetradecyl trimethyl pyridinium salts, hexadecyl trimethyl pyridinium salts and the like.

The concentration of the cationic surfactant may be 10 to 50000 mg/ml, preferably 100 to 3000 mg/ml.

No particular limitation is given to the anionic surfactant, but are suitably used N-acylaminoacetic acid salts such as lauroyl sarcosinate, cocoyl sarcosinate, myristoyl sarcosinate and oleyl sarcosinate.

The concentration of the anionic surfactant may be 0.1 to 10 mg/ml, preferably 0.5 to 5 mg/ml.

No particular limitation is given to the ampholytic surfactant, but are suitably used carboxy betaine of the following formula:

wherein $R^{14}$ is a $C_{8-20}$ alkyl group; $R^{15}$ and $R^{16}$, the same or different, are a $C_{1-3}$ alkyl group, a $C_{2-3}$ alkenyl or alkynyl group.

The $C_{1-3}$ alkyl group may be the same as mentioned above. The $C_{2-3}$ alkenyl group may be vinyl, allyl. The $C_{2-3}$ alkynyl group may be acetylenyl, propynyl. The $C_{8-20}$ alkyl group may be octyl, decyl, dodecy, tetradecyl or the like.

For example, may be mentioned dodecyl dimethyl betaine, hexadecyl dimethyl betaine, decyl dimethyl betaine and the like.

The concentration of the ampholytic surfactant may be 1 to 100 mg/ml, preferably 5 to 20 mg/ml.

No particular limitation is given to the nonionic surfactant, but are suitably used polyoxyethylene(n)alkyl ethers wherein the alkyl group has a carbon number of 10 to 20 and n is from 10 to 20 and polyoxyethylene(n)alkylphenyl ethers wherein the alkyl group has a carbon number of 8 to 10 and n is from 2 to 20 such as POE(10)octylphenyl ether.

Other surfactants recognized as having the characteristic of solubilizing membrane protein include Triton X-100 (polyethylene glycol mono[p-(1,1,3,3,-tetramethylbuty)phenyl] ether), CHAPS (3-[(3-cholamidopropyl)dimethylammonio] propanesulfonic acid], CHAPSO (3-[(3-cholamidopropyl) dimethylammonio]-2-hydroxypropanesulfonic acid), BIGCHAP (N,N-bis(3-D-gluconamidopropyl)cholamide), deoxy-BIGCHAP (N,N-bis(3-D-gluconamidopropyl)deoxycholamide), sucrose monocaprate, sucrose monocholate, n-octyl-α-D-glucopyranoside, n-heptyl-α-D-thioglucopyranoside, n-octyl-α-D-thioglucopyranoside, n-dodecyl-α-Dmaltopyranoside, n-nonyl-α-D-thiomaltopyranoside and the like.

The concentration of these surfactants may be 0.5 to 50 mg/ml, preferably 1.0 to 10 mg/ml.

Further, besides the surfactants, anti-bacterial/antiseptic agents (anti-bacterial agents) and the like may be mentioned. As examples of the agents, are suitably used isothiazoline containing anti-bacterial agents and biguanide containing antiseptic agents. The concentration of the agent may suitably be 1.0 to 30 mg/ml.

The organic solvent such as alcohol may be methanol, ethanol, isobutyl alcohol, phenoxy ethanol, methoxy ethanol, ethoxy ethanol, butoxy ethanol or the like. The concentration of these alcohols may suitably be 1.0 to 100 mg/ml.

The dye is not particularly limited as long as it can stain bacteria. Where a urine sample is examined, a dye capable of staining bacteria under an acidic state is preferably used. The concentration thereof may suitably be determined depending on the kind of dye, for example, in the range of 0.1 to 100 ppm (final concentration). In view of bacteria detectability, a fluorescent dye which is at least bonded to one of components constituting bacteria and emits fluorescent light is advantageously used. From this point of view, polymethine dyes are preferable. For example, the following dyes (1) to (11) are used:

Thiazole Orange; (1)

ClO$_4^-$ (2)

ClO$_4^-$ (3)

3 Br$^-$ (4)

(5)

(6)

2 I$^-$ (7)

2(CH$_3$CH$_2$)$_3$NH$^+$

(8)

(9)

-continued (10)

a compound represented by the following general formula:

wherein $R_1$ is a hydrogen atom or a $C_{1-3}$ alkyl group; $R_2$ and $R_3$ are a hydrogen atom, a $C_{1-3}$ alkyl group or a $C_{1-3}$ alkoxy group; $R_4$ is a hydrogen atom, an acyl group or a $C_{1-3}$ alkyl group; $R_5$ is a hydrogen atom or a $C_{1-3}$ alkyl group which may be substituted; Z is a sulfur atom, an oxygen atom or a carbon atom substituted with a $C_{1-3}$ alkyl group; n is 1 or 2; $X^-$ is an anion; and wherein $R^6$ is a hydrogen atom or a $C_{1-18}$ alkyl group; $R^7$ and $R^8$ are a hydrogen atom, a $C_{1-3}$ alkyl group or a $C_{1-3}$ alkoxy group; $R^9$ is a hydrogen atom, an acyl group or a $C_{1-18}$ alkyl group; Z is sulfur, oxygen or a carbon atom substituted with a $C_{1-3}$ alkyl group; n is 0, 1 or 2; $X^-$ is an anion.

The $C_{1-3}$ alkyl group may be methyl, ethyl, propyl and the like. The $C_{1-18}$ alkyl group may be methyl, ethyl, propyl, octyl, decyl, dodecyl, tetradecyl and the like. The a $C_{1-3}$ alkoxy group may be methoxy, ethoxy, propoxy and the like. Substituents to the $C_{1-3}$ alkyl group may be a hydroxyl group, a halogen atom and the like.

Among the above-mentioned dyes, (1) is commercially available. (2) and (3) are supplied by Nippon Photosensitive Dye Laboratory Ltd., and (5) to (9) are supplied by Molecular Probes, Inc. Manufacturing methods of (10) and (11) are described in Japanese Unexamined Patent Publications Nos. Hei 9(1997)-104683 and Hei 10(1998)-319010, respectively.

Among the dyes (10), a dye represented by the formula:

is particularly suitable.

Further, among the dyes (11), a dye represented by the formula:

is particularly suitable.

In the present invention, pH at the staining step is not specifically limited as long as it allows the bacteria staining. Where a urine sample is stained at an acidic pH, (1) bacteria is stained better than in a neutral or alkaline state and (2) nonspecific staining of mucus threads is prevented and the mucus threads is lysed to a certain extent. Thus, the acidic state is advantageous to the bacteria staining.

A buffer of pKa 1 to 5.5 is used to maintain the acidic state. The buffer is not particularly limited, but an acid or a compound capable of maintaining pH 2.0-3.0 may be used. As the buffer, it may be utilized one or more kinds of compounds selected from the group comprising of: citric acid or its salts, phosphoric acid or its salts, phthalic acid or its salts, succinic acid or its salts, lactic acid or its salts, ε-aminocaproic acid or its salts, fumaric acid or its salts, β-alanine, glycine and the like. The salts described above include alkali or alkaline earth salts. Suitable examples thereof is at least one selected from the group consisting of: citric acid-NaOH, potassium dihydrogen phosphate-disodium hydrogen phosphate, potassium dihydrogen phosphate-NaOH, citric acid-disodium hydrogen phosphate, potassium hydrogen phthalate-NaOH, succinic acid-NaOH, lactic acid-NaOH, ε-aminocaproic acid-HCl, fumaric acid-HCl, β-alanine-NaOH, glycine-NaOH and the like. Appropriate use amount thereof is such that the above-mentioned pH range is maintained, preferably about 10 to 500 mM in the sample.

Further, where a urine sample is examined, the staining is carried out by further utilizing an inorganic salt of either sulfate or nitrate. This is preferable since fluorescent dye transmissivity of bacteria is enhanced and nonspecific staining of contaminants is prevented. The inorganic salt may be used in a concentration of about 10 to 500 mM, preferably about 50 to 200 mM in the sample.

In the present invention, the working a dye on a sample (staining) may be carried out by mixing the sample, one by one or simultaneously, an aqueous solution containing the substance capable of reducing nitrite ions and/or the cationic surfactant and a solution containing the dye. The dye may be contained in the aqueous solution containing the substance capable of reducing nitrite ions and/or the cationic surfactant. However, where the dye to be utilized is unstable in the aqueous solution, it may be dissolved in a water-soluble organic solvent such as methanol, ethanol or ethylene glycol and then mixed for use with the aqueous solution containing the substance capable of reducing nitrite ions and/or the cationic surfactant. This improves storage stability of the dye.

Temperature and time for the staining are not particularly limited, but the staining may be performed at about 15 to 50° C. for about 20 minutes or less, preferably about 15 minutes or less, more preferably about 15 minutes immediately after the mixing.

The sample stained by the method of the present invention may be observed with a microscope or an imaging apparatus to detect bacteria. Alternatively, bacteria can be detected and counted by using a flow cytometer with high accuracy. The flow cytometer used herein may be a commercially available apparatus generally utilized in the art.

That is, the method of detecting and counting bacteria according to the present invention is carried out by the steps of:
(1) working a dye for staining bacteria on a sample by the method as described above,
(2) introducing the thus treated sample into a detecting part of a flow cytometer and irradiating cells of the stained bacteria one by one with light to measure scattered light and fluorescent light emitted from each of the cells; and
(3) discriminating the bacteria from other components in accordance with an intensity of a scattered light signal and an intensity of a fluorescent light signal or a pulse width reflecting the length of particles to count the bacteria.

The method of working the dye on the sample may be performed as described above, e.g., by mixing a sample with an aqueous solution containing a substance capable of reducing nitrite ions and/or a cationic surfactant to accelerate dye transmissivity of bacteria and then (or simultaneously) staining the sample for a certain period with a dye.

Figure 4:
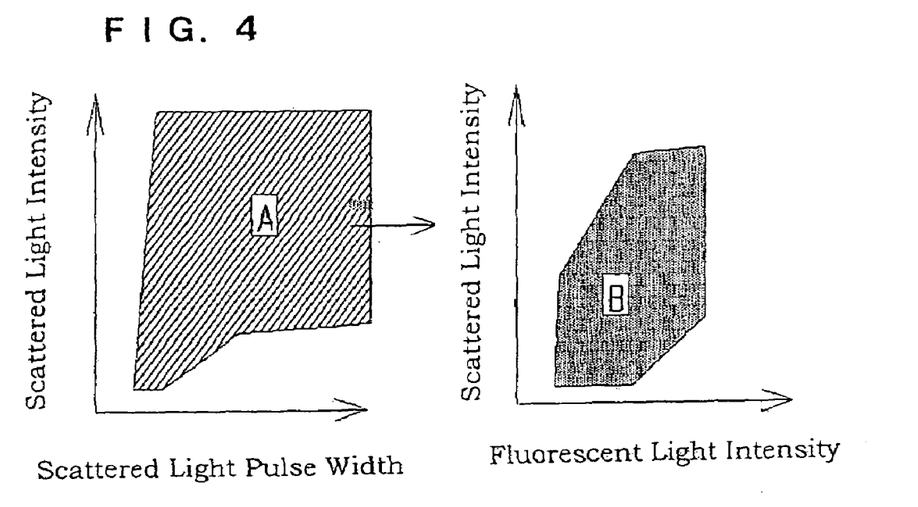
FIG. 4 is a view illustrating the outline of the method of detecting bacteria according to the present invention.

Discrimination of bacteria from other components and counting of bacteria are carried out in accordance with combination of signals obtained by using a flow cytometer. Example of the combination includes, for example, a forward scattered light intensity and a forward scattered light pulse width, a forward scattered light intensity and a fluorescent light intensity, a forward scattered light pulse width and a fluorescent light intensity, and the like. In a suitable manner, for example, firstly, a scattergram is formed from the combination of the forward scattered light intensity and the forward scattered light pulse width, and then gating is performed to a mass including bacteria specified on the scattergram to separate mucus threads, mainly. Further, another scattergram is formed from the forward scattered light intensity and the fluorescent light intensity of the gated mass to separate bacteria from other components (crystals, cell fragments and the like) based on the difference in the fluorescent light intensity. The outline of the method is shown in FIG. 4. Where the sample contains bacteria only, a scattergram is formed from the forward scattered light intensity and the fluorescent light intensity to count them.

EXAMPLES

Hereinafter, preferred examples of the method of staining and detecting bacteria according to the present invention are described, but the present invention is not limited thereto.

Example 1

Reagent Composition (Diluent)

| | |
|---|---|
| Citric acid | 92.3 mM |
| Sodium hydroxide | 0.75 g/l (up to pH 2.5) |
| Tetradecyl trimethyl ammonium bromide | 0.1% (w/v) |
| Sodium sulfate | 90 mM |
| Ascorbic acid | 85 mM |

(Staining Solution)

Dye A (of the Following Structural Formula) 40 ppm (in Ethylene Glycol)

Figure 1:
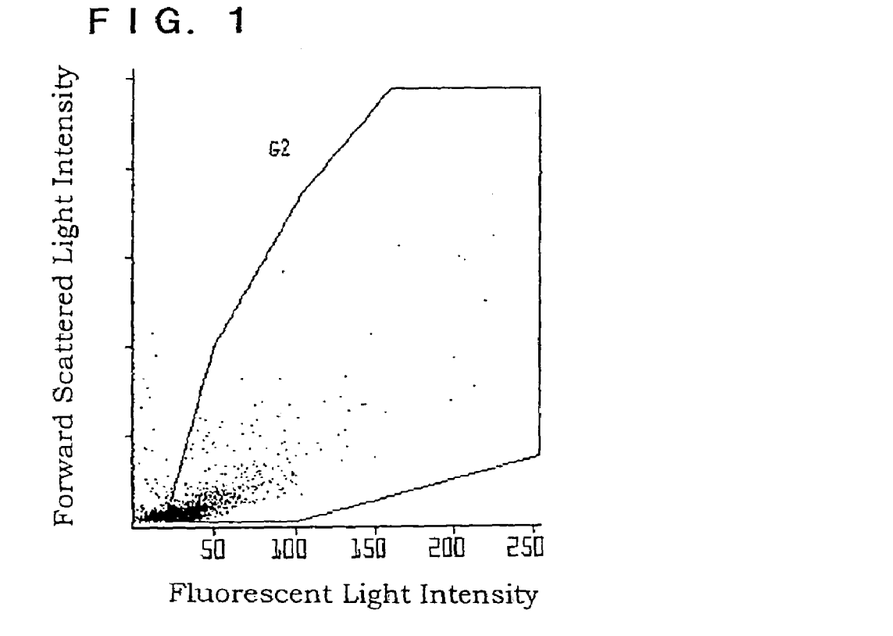
FIG. 1 is a scattergram of a fluorescent light intensity—a forward scattered light intensity obtained in the case where ascorbic acid is used as a reducing agent in Example 1 of the present invention.
Figure 2:
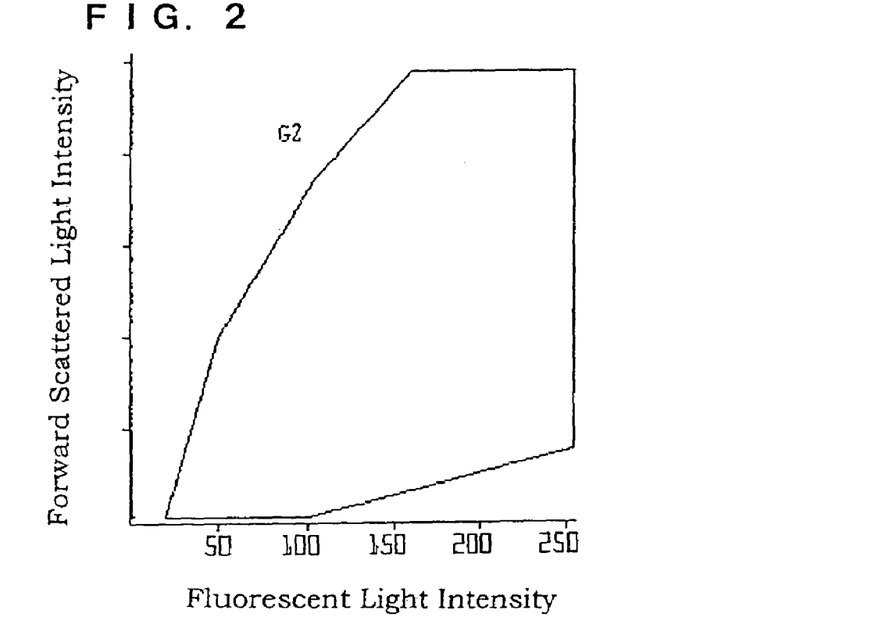
FIG. 2 is a scattergram of a fluorescent light intensity—a forward scattered light intensity obtained in the case where the reducing agent is not used in Example 1 of the present invention.

To 140 μl of a sample containing a large amount of nitrite ions (bacteria concentration of $5.0 \times 10^6$/ml; hospital urine), 952 μl of the above-mentioned diluent was added and the staining solution was added so that the final concentration of the dye A would be 1 ppm. Staining was carried out at 40° C. for 20 seconds and then scattered light and fluorescent light were measured by a flow cytometer provided with a red semiconductor laser as a light source (amount of examined urine: 8.0 μl). Then, as shown in FIG. 1, a scattergram was formed with a fluorescent light intensity (FLI) as an horizontal axis and a forward scattered light intensity (FSLI) as a vertical axis. As a control, measurement was performed using a reagent containing no ascorbic acid (FIG. 2).

In the case where the reagent without ascorbic acid was used, bacteria were not stained and the fluorescent light intensity was zero. In contrast, bacteria were stained and detected when ascorbic acid was added.

Example 2

Figure 3:
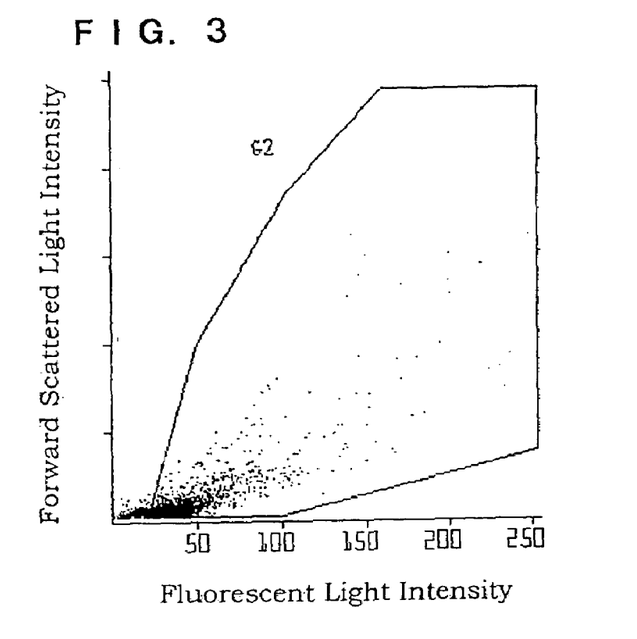
FIG. 3 is a scattergram of a fluorescent light intensity—a forward scattered light intensity obtained in the case where sulfamic acid is used as the reducing agent in Example 2 of the present invention.

Measurement was performed in the same manner as in Example 1 except that sulfamic acid of 100 mM was used instead of ascorbic acid in the diluent. FIG. 3 shows the results. Bacteria were stained and detected as in Example 1.

According to the method of staining bacteria of the present invention, the substance capable of reducing nitrite ions and/or the cationic surfactant are added. Therefore, dye transmissivity to the bacteria cells is enhanced even if nitrate-reducing bacteria produce nitrite ions in the sample, so that bacteria can be quickly detected with high accuracy. Further, since bacteria are stained in an aqueous state, dry fixation such as Gram staining is not necessarily required. Therefore, staining period can be remarkably reduced and thus a sample for measurement can be prepared in a short time including the staining step.

Since the staining according to the present invention can easily be performed by merely mixing the sample and the reagent, skill required in Gram staining is eliminated. Further, the staining step can be easily carried out, which facilitates the automation through the staining step to the measurement step (such as flow cytometry and image analysis).

According to the method of detecting bacteria of the present invention, bacteria can be counted with high accuracy without being affected by the contaminants. Specifically, bacteria of $10^4$/ml can be counted.

Further, bacteria whose growth is difficult on medium (bacteriostatic samples) can also be counted reliably.

What is claimed is:

1. A method of preparing an assay sample for detecting bacteria by a flow cytometer, comprising:
   providing a diluent comprising a cationic surfactant, a buffer for maintaining a pH of 2.0-4.5 and an effective amount of a substance capable of reducing nitrite ions and a staining solution comprising a polymethine dye for staining bacteria;
   mixing a urine sample with the diluent; and
   preparing the assay sample by mixing the mixture of the urine sample and the diluent with the staining solution;

wherein the polymethine dye is at least one selected from the following group consisting of:

(1) Thiazole Orange;

wherein $R_1$ is a hydrogen atom or a $C_{1-3}$ alkyl group; $R_2$— and $R_3$ are a hydrogen atom, a $C_{1-3}$ alkyl group or a $C_{1-3}$ alkoxy group; $R_4$ is a hydrogen atom, an acyl group or a $C_{1-3}$ alkyl group; $R_5$ is a hydrogen atom or a $C_{1-3}$ alkyl group which may be substituted; Z is a sulfur atom, an oxygen atom or a carbon atom substituted with a $C_{1-3}$ alkyl group; n is 1 or 2; X is an anion; and (11) a compound represented by the following general formula:

wherein $R_6$ is a hydrogen atom or a $C_{1-18}$ alkyl group; $R_7$ and $R_8$ are a hydrogen atom, a $C_{1-3}$ alkyl group or a $C_{1-3}$ alkoxy group; $R_9$ is a hydrogen atom, an acyl group or a $C_{1-18}$ alkyl group; Z is sulfur, oxygen or a carbon atom having a $C_{1-3}$ alkyl group; n is 0, 1 or 2; $X^-$ is an anion; and wherein the cationic surfactant is a quaternary ammonium salt represented by the following formula:

wherein $R^{10}$ is a $C_{6-18}$ alkyl group or a benzyl group; $R^{11}$, $R^{12}$ and $R^{13}$, the same or different, are a $C_{1-3}$ alkyl group or a benzyl group; $Y^-$ is a halogen ion.

2. The method according to claim 1, wherein the substance capable of reducing nitrite ions is selected from the group consisting of: ascorbic acid, isoascorbic acid, aminomethanesulfonic acid, aminoethanesulfonic acid, glutamic acid, asparatic acid, mercaptoacetic acid, 3-mercaptopropionic acid, sulfamic acid, sulfanilic acid, sulfurous acid, pyrosulfurous acid, phosphinic acid, glycine, glutamine, asparagine, methionine, glutathione, cysteine, hydroxylamine and salts thereof; sulfanilamide; aminomethane; mercaptoethanol; thiophenol and urea.

3. The method according to claim 1, wherein the quaternary ammonium salt is at least one selected from the group consisting of: decyl trimethyl ammonium salt, dodecyl trimethyl ammonium salt, tetradecyl trimethyl ammonium salt, hexadecyl trimethyl ammonium salt and octadecyl trimethyl ammonium salt.

4. The method according to claim 1, wherein the diluent has pH of 2.0-3.0.

5. The method according to claim 1, wherein the buffer is at least one selected from the group consisting of: citric acid-NaOH, potassium dihydrogen phosphate-disodium hydrogen phosphate, potassium dihydrogen phosphate-NaOH, citric acid-disodium hydrogen phosphate, potassium hydrogen phthalate-NaOH, succinic acid-NaOH, lactic acid-NaOH, ε-aminocaproic acid-HCl, fumaric acid-HCl, β-alanine-NaOH and glycine-NaOH.

6. The method according to claim 1, wherein the diluent comprises an inorganic salt of either sulfate or nitrate.

7. The method according to claim 1, wherein the dye is present at 0.1 to 100 ppm in the assay sample.

8. The method according to claim 1, wherein the cationic surfactant exists at 10 to 30000 mg/l in the assay sample.

9. The method according to claim 1, wherein the staining solution comprises a water-soluble organic solvent.

10. The method according to claim 9, wherein the water-soluble organic solvent is selected from the group consisting of methanol, ethanol and ethylene glycol.

11. The method according to claim 9, wherein the water-soluble organic solvent comprises ethylene glycol.

12. A method of staining bacteria comprising:
providing a diluent comprising a cationic surfactant, a buffer for maintaining a pH of 2.0-4.5 and an effective amount of a substance capable of reducing nitrite ions and a staining solution comprising a polymethine dye for staining bacteria;
mixing a urine sample with the diluent; and
mixing the mixture of the urine sample and the diluent with the staining solution;

wherein the polymethine dye is at least one selected from the following group consisting of:

(1) Thiazole Orange;

-continued (8)

(9)

(10)

a compound represented by the following general formula:

wherein $R_1$ is a hydrogen atom or a $C_{1-3}$ alkyl group; $R_2$— and $R_3$ are a hydrogen atom, a $C_{1-3}$ alkyl group or a $C_{1-3}$ alkoxy group; $R_4$ is a hydrogen atom, an acyl group or a $C_{1-3}$ alkyl group; $R_5$ is a hydrogen atom or a $C_{1-3}$ alkyl group which may be substituted; Z is a sulfur atom, an oxygen atom or a carbon atom substituted with a $C_{1-3}$ alkyl group; n is 1 or 2; X is an anion; and (11) a compound represented by the following general formula:

wherein $R_6$ is a hydrogen atom or a $C_{1-18}$ alkyl group; $R_7$ and $R_8$ are a hydrogen atom, a $C_{1-3}$ alkyl group or a $C_{1-3}$ alkoxy group; $R_9$ is a hydrogen atom, an acyl group or a $C_{1-18}$ alkyl group; Z is sulfur, oxygen or a carbon atom having a $C_{1-3}$ alkyl group; n is 0, 1 or 2; $X^-$ is an anion; and wherein the cationic surfactant is a quaternary ammonium salt represented by the following formula:

$$R^{11}-\underset{\underset{R^{12}}{|}}{\overset{\overset{R^{10}}{|}}{N^+}}-R^{13} \quad Y^-$$

wherein $R^{10}$ is a $C_{6-18}$ alkyl group or a benzyl group; $R^{11}$, $R^{12}$ and $R^{13}$, the same or different, are a $C_{1-3}$ alkyl group or a benzyl group; $Y^-$ is a halogen ion.

* * * * *

UNITED STATES PATENT AND TRADEMARK OFFICE
CERTIFICATE OF CORRECTION

PATENT NO. : 7,645,594 B2
APPLICATION NO. : 10/803667
DATED : January 12, 2010
INVENTOR(S) : Sakai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 925 days.

Signed and Sealed this

Sixteenth Day of November, 2010

David J. Kappos
*Director of the United States Patent and Trademark Office*